(12) United States Patent
Gardner et al.

(10) Patent No.: US 6,838,235 B2
(45) Date of Patent: Jan. 4, 2005

(54) METHODS FOR IN VITRO FERTILIZATION

(75) Inventors: David K. Gardner, Highlands Ranch, CO (US); Michelle Lane, Highlands Ranch, CO (US)

(73) Assignee: Vitrolife Group, Gothenburg (SE)

( * ) Notice: Subject to any disclaimer, the term of this patent is extended or adjusted under 35 U.S.C. 154(b) by 53 days.

(21) Appl. No.: 10/322,914

(22) Filed: Dec. 18, 2002

(65) Prior Publication Data
US 2003/0091972 A1 May 15, 2003

Related U.S. Application Data

(63) Continuation-in-part of application No. 09/201,594, filed on Nov. 30, 1998, now abandoned.

(51) Int. Cl.$^7$ .............................. A01N 1/02; C12N 5/08
(52) U.S. Cl. .......................... 435/2; 435/366; 435/374; 435/404
(58) Field of Search ........................... 435/2, 366, 374, 435/404

(56) References Cited

U.S. PATENT DOCUMENTS

| | | |
|---|---|---|
| 4,007,087 A | 2/1977 | Ericsson |
| 4,327,177 A | 4/1982 | Shrimpton |
| 4,804,537 A | 2/1989 | Bergman |
| 5,096,822 A | 3/1992 | Rosendrans, Jr. et al. |
| 5,432,160 A | 7/1995 | Hara et al. |
| 5,496,720 A | 3/1996 | Susko-Parrish et al. |
| 6,010,448 A | 1/2000 | Thompson |
| 6,130,086 A | 10/2000 | Nakazawa et al. |

FOREIGN PATENT DOCUMENTS

| | | |
|---|---|---|
| CA | 2199663 | 9/1998 |
| EP | 86109103.1 | 7/1986 |
| EP | 92305952.1 | 6/1992 |
| EP | 0872 80 A1 | 10/1998 |
| WO | WO 86/07377 | 12/1986 |
| WO | WO 99/67364 | 12/1999 |

OTHER PUBLICATIONS

Quinn et al., "Improved Pregnancy Rate in Human In Vitro Fertilization with the Use of a Medium Based on the Composition of Human Tubal Fluid," *Fertility and Sterility*, 44, pp. 493–498, 1985; published by Elsevier Science, New York.

E. Roth et al., "Influence of Two Glutamine–Containing Dipeptides on Growth of Mammalian Cells," *In Vitro Cellular & Devel Biol.* 24 (7), pp. 696–698; 1988; published by Tissue Culture Assoc, Inc.

Jones et al., "Evolution of a Culture Protocol for Successful Blastocyst Development and Pregnancy," *Human Repro* 88, pp. 361–368, 1990; published by Journals of Reproduction & Fertility Ltd., Cambridge.

Gardner et al., "Concentrations of Nutrients in Mouse Oviduct Fluid and Their Effects on Embryo Development and Metabolism In Vitro," *J. Repro & Fertility 88*, pp. 361–368, 1990; published by Journals of Reproduction & Fertility Ltd., Cambridge.

D. G. Hammitt et al., "Improved Methods for Preparation of Culture Media for in–vitro Fertilization and Gamete Intra–Fallopian Transfer" *Human Repro 5* (4), pp. 457–463, 1990.

H. J. Leese, "The Environment of the Preimplantation Embryo" from *Establishing a Successful Human Pregnancy*, in *Serono Symposia Publications from Raven Press 66*, pp. 143–154, 1990; R. G. Edwards, editor.

J. Yovich and G. Grudzinskas, from *The Management of Infertility. A Manual of Gamete Handling Procedures*, Heinemann Professional Publishing, Ltd., pp. 106–195, 1990.

Lane et al., "Effect of Incubation Volume and Embryo Density on the Development and Viability of Mouse Embryos In Vitro," *Human Repro 7*, pp. 558–562, 1992; published by Oxford Univ. Press, Oxford.

Gardner et al., Mouse Embryo Cleavage, Metabolism and Viability: Role of Medium Composition, *Human Repro 8*, pp. 288–295, 1993; published by Oxford Univ. Press, Oxford.

Gardner et al., "Embryo Culture Systems," *Handbook of in vitro Fertilization*, A.O. Trounson & D.K. Gardner, eds., pp. 85–114, 1993; published by CRC Press, Boca Raton, FL.

Gardner et al., "Amino Acids and Ammonium Regulate Mouse Embryo Development in Culture," *Biol. Repro 48*, pp. 377–385, 1993; published by the Society for the Study of Reproduction, Madison, WI.

Lane et al., "Increase in Postimplantation Development of Cultured Mouse Embryos by Amino Acids and Induction of Fetal Retardation and Exencephaly by Ammonium Ions," *J Repro & Fertility 102*, pp. 305–312, 1994; published by Journals of Reprodcution & Fertility Ltd., Cambridge.

(List continued on next page.)

Primary Examiner—Christopher R. Tate
(74) Attorney, Agent, or Firm—Foley & Lardner

(57) ABSTRACT

Instead of immersing human reproductive cells in a single culture medium throughout the various procedures used in IVF, a process is provided by which the reproductive cells may be moved through a sequence of distinct culture media as the various IVF procedures are carried out. In one implementation, the culture media specifically formulated to provide a physical environment similar to that found within the female reproductive tract and conducive to growth and development of human reproductive cells during the various stages of the IVF process. In this regard, specifically formulated culture media can be applied to support the reproductive cells in one or more of the following procedures: oocyte retrieval and handling; oocyte maturation; ordinary fertilization; oocyte, zygote and embryo examination and biopsy; embryonic development to the eight-cell stage; embryonic development to the blastocyst stage; embryo transfer; and cryopreservation.

19 Claims, 1 Drawing Sheet

OTHER PUBLICATIONS

Gardner et al., "Enhanced Rates of Cleavage and Development for Sheep Zygotes Cultured to the Blastocyst Stage in Vitro in the Absence of Serum and Somatic Cells: Amino Acids, Vitamins, and Culturing Embryos in Groups Stimulate Development," *Biol Repro 50*, pp. 390–400, 1994; published by the Society for the Study of Reproduction, Madison, WI.

Gardner, David K., "Mammalian Embryo Culture in the Absence of Serum or Somatic Cell Support," *Cell Biol. Int'l 18*, pp. 1163–1179, 1994; published by Academic Press, London.

Barnes et al., "Blastocyst Development and Birth After In–Vitro Maturation of Human Primary Oocytes, Intracytoplasmic Sperm Injection and Assisted Hatching," *Human Repro*, pp. 3243–3247, 1995; published by Oxford Univ. Press, Oxford.

Gardner et al., "Alleviation of the '2–Cell Block' and Development to the Blastocyst of CFI Mouse Embryos: Role of Amino Acids, EDTA and Physical Parameters," *Human Repro 11*, pp. 2703–2712, 1996; published by Oxford Univ. Press, Oxford.

J.K. O'Brien et al., "Development Capacity, Energy Metabolism and Ultrastructure of Mature Oocytes from Prepubertal and Adult Sheep" *Repro Fertil Devel 8*, pp. 1029–1037, 1996.

R.D. Schramm et al., "Development of in–vitro–fertilized Primate Embryos into Blastocysts in a Chemically Defined, Protein–Free Culture Medium," *Human Repro 11*, (8), pp. 1690–1697, 1996; published by European Society for Human Reproduction and Embryology.

Gardner et al., "Complex Physiologically Based Serum–Free Culture Media Increase Mammalian Embryo Development", pp. 187–191, 1997.

Gardner et al., "Culture and Selection of Viable Blastocysts; A Feasible Proposition for Human IVF?," *Human Repro Update 3*, pp. 367–382, 1997; published by Oxford Univ. Press, Oxford.

Lane et al., "Differential Regulation of Mouse Embryo Development and Viability by Amino Acids," *J Repro & Fertility 109*, pp. 153–164, 1997; published by Journals of Reproduction & Fertility Ltd., Cambridge.

Lane et al., "Nonessential Amino Acids and Glutamine Decrease the Time of the First Three Cleavage Divisions and Increase Compaction of Mouse Zygotes In Vitro," *J Assisted Repro and Genetics 14*, pp. 398–403, 1997; published by Kluwer, New York.

Abeyderra et al., Fertilization ant Subsequent Development in vitro of Pig Oocytes Inseminated in a Modified Tris–Buffered Medium with Frozen–hawed Ejaculated Spermatozoa, *Biol Repro 57*, pp. 729–734, 1997.

Keskintepe et al., Caprine Blastocyst Formation Intracytoplasmic Sperm Injection and Defined Culture, *Zygote 5* (3), pp. 261–265, 1997.

Gardner et al., "Culture and Transfer of Human Blastocysts Increases Implantation Rates and Reduces the Need for Multiple Embryo Transfers," *Fertility and Sterility 69*, pp. 84–88, 1998; published by Elsevier Science, New York.

D. Gardner, "Development of Serum–Free Media for the Culture and Transfer of Human Blastocysts," *Human Repro 13*, pp. 101–108, 1998; published by Oxford Univ. Press, Oxford.

Gardner et al., "Elimination of High–Order, Multiple Gestations by Blastocyst Culture and Transfer," *Female Infertility Therapy: Current Practice,* Z. Shoham et al., eds., pp. 267–274, 1998; published by Martin Dunnitz, London.

D. Gardner, "Improving Embryo Culture and Enhancing Pregnancy Rate," *Female Infertility Therapy: Current Practice,* Z. Shoham et al., eds., pp. 283–299, 1998; published by Martin Dunnitz, London.

Gardner et al., "Human Embryo Viability: What Determines Developmental Potential, and Can It Be Assessed?," *J Assisted Repro & Genetics 15*, pp. 455–458, 1998; published by Kluwer, New York.

D. Gardner, "Changes in Requirements and Utilization of Nutrients During Mammalian Preimplantation Embryo Development and Their Significance in Embryo Culture," *Theriogenology 49*, pp. 83–102, 1998; published by Elsevier Science, New York.

Gardner et al., "Culture of Viable Human Blastocysts in Defined Sequential Serum–Free Media," *Human Repro 13*, pp. 148–159, 1998; published by Oxford Univ. Press, Oxford.

Lane et al., "Amino Acids and Vitamins Prevent Culture––Induced Metabolic Perturbations and Associated Loss of Viability of Mouse Blastocysts," *Human Repro 13*, pp. 991–997, 1998; published by Oxford Univ. Press, Oxford.

D. Gardner, "Embryo Development and Culture Techniques," *Animal Breeding. Technology for the 21$^{st}$ Century,* A. J. Clark, ed., pp. 13–46, 1998; published by Harwood Academic Publishers, Amsterdam.

Jones et al., Evolution of a Culture Procotol for Successful Blastocyst Development and Pregnancy, 13:169–177, 1988.

METHODS FOR IN VITRO FERTILIZATION

FIELD OF THE INVENTION

The present invention relates generally to human in vitro fertilization (IVF) and, in particular, to a sequential culture media system and process to be used in oocyte retrieval, handling and maturation, sperm preparation, fertilization, embryo development and transfer, and cryopreservation. The invention provides the gametes, zygote and developing embryo with a physical environment adapted to their physiological needs, so supporting their normal growth and development in vitro and increasing the likelihood of successful pregnancy.

BACKGROUND OF THE INVENTION

In vitro fertilization seeks to duplicate, to a large extent, the conditions and processes normally occurring within the female reproductive system that are necessary to oocyte development, fertilization and early embryonic development. In the clinic and laboratory, IVF involves several discrete procedures, such as collection of the oocytes from the ovary of the mother, preparation of the sperm, fertilization, and, once fertilized eggs are identified, a period of early embryonic development, and then transfer of the embryo to the mother's uterus. Each of these steps can take place over extended periods of time, during which the individual cells involved have a continuing need for nutrients, and are subjected to significant stress as a result of clinical manipulation and changed environmental conditions.

During IVF, a culture medium is ordinarily used as a substitute for the fluid secreted by the female reproductive tract that would ordinarily surround the gametes, zygote, and developing embryo. Most laboratories carrying out IVF use a single culture medium throughout the various procedures involved. In a number of laboratories, there has been a tendency to use tissue culture media for IVF procedures, such as Ham's F-10, which is formulated to support somatic cell growth, not gamete or embryonic cell growth. Tissue culture media generally are complicated systems, containing an array of amino acids, vitamins and other constituents. They can contain components that significantly impair embryonic development and viability after transfer. Further, to the extent tissue culture media contain components that are generally needed by the gametes and the embryo, the media are not formulated to provide the components at levels appropriate to support healthy gamete and embryonic development.

Other laboratories have used simple culture media, consisting of balanced salt solutions supplemented with carbohydrate energy sources such as glucose, pyruvate and lactate. Examples include Earle's, T-6, and human tubal fluid (HTF). These media generally lack certain key components found in the female reproductive tract, such as non-essential amino acids, and their constituents are not formulated in concentrations that meet the specific changing needs of the gametes and developing embryo at various stages of their development.

The two types of culture media commonly used for IVF generally are only capable of supporting embryonic development to the eight-cell stage. Such media are ordinarily not capable of supporting and producing a viable blastocyst stage embryo, complete with an epithelium and competent inner cell mass. Accordingly, embryo transfer, the return of the fertilized oocyte to the uterus of the mother, usually occurs at around the four-cell stage (day two) or around the eight-cell stage (day three). This is a time when the four- or eight-cell embryo would not typically have arrived in the uterus of the mother, if fertilization had occurred in vivo. Embryo transfer at this time involves placing the cleavage stage embryo in an environment oriented to a blastocyst stage embryo. The cleavage stage embryo must then undergo further development in a non-homologous environment to reach the blastocyst stage, in which the embryo has trophectoderm cells capable of implanting in the uterine lining.

Recent research and human trials have led to the development of two new culture media, G1 and G2, which represent significant advancements in adaptation of culture media to the physiological needs of the cleavage stage embryo and the embryo in the eight-cell through blastocyst stage of development. These media are described in the following publications: Barnes, Crombie, Gardner, et al, Blastocyst Development and Birth After In-vitro Maturation of Human Primary Oocytes, Intracytoplasmic Sperm Injection and Assisted Hatching, Human Reproduction, vol. 10, no. 12, pp. 3243–47 (December, 1995); Gardner and Lane, Culture and Selection of Viable Blastocysts: A Feasible Proposition for Human IVF?, Human Reproduction Update, Vol. 3, No. 4, pp. 367–82 (1997); Gardner, Vella, Lane, et al, Culture and Transfer of Human Blastocysts Increases Implantation Rates and Reduces the Need for Multiple Embryo Transfers, Fertility and Sterility, Vol. 69, No. 1, pp. 84–88 (January 1998). Use of these media, and particularly the G2 medium, supports the growth and development of viable blastocyst stage embryos in vitro. Accordingly, the development of these media paves the way for new approaches to embryo transfer to the uterus at the blastocyst stage, when the embryo is most adapted to surviving in the uterine environment and has developed structures and capabilities required for implantation to take place. Research utilizing the G1 and G2 media, and embryo transfer at the blastocyst stage, suggests that these media contribute to higher pregnancy rates, and reduces the need for transfer of multiple embryos and the risk of multiple births. Neither of these media, however, is optimized for supporting the gametes, oocyte maturation, or fertilization.

SUMMARY OF THE INVENTION

It has been recognized that IVF processes may be improved by providing specific media and media sequences for supporting gametes, zygotes and developing embryos relative to various phases of the IVF process. In certain respects, such media and sequences better reflect in vivo development. Within the female reproductive system, the oocyte is developed within and released from the ovary during ovulation, and proceeds through the oviduct towards the uterus. During this journey, it experiences a dynamic physical environment. The fluid of the oviduct contains a number of components that provide nourishment to the oocyte and its surrounding cumulus cells, and that also appear to interact with the oocyte and its cumulus cells, so stimulating development. Similarly, the fluid of the female reproductive tract provides nourishment to sperm traveling through the oviduct, and also stimulates certain changes in the sperm necessary to fertilization. Once fertilization occurs, the resulting zygote travels down the oviduct and enters the uterus approximately three days later, undergoing internal transformation and experiencing a changing environment.

As the zygote travels, cell division, or cleavage, occurs as well as significant developmental changes. The cells of early embryonic development have different capabilities and nutritional needs from those of later embryonic development prior to implantation. The zygote and cleavage stage embryo (up to the eight-cell stage) are characterized by low levels of biosynthesis, low respiratory rates, only limited ability to metabolize glucose, and a capacity to utilize pyruvate. As the embryo develops, and genome activation occurs, the embryo gains an increased capacity to utilize glucose. At the blastocyst stage of development, when the embryo is entering and within the uterus, the embryo's metabolic system has developed and the embryo has a substantially greater capacity to use and need for glucose, and less need for pyruvate. The makeup of the fluid surrounding the developing embryo in the female reproductive tract seems to be tailored to these changing needs: in the oviduct at the time when the oocyte and developing embryo are present, relatively low levels of glucose are found, while pyruvate concentrations are high; at the time the embryo enters the uterus, glucose reaches its highest level and the pyruvate concentration is comparatively low. Cleavage stage embryos, like the oocyte, are susceptible to loss of amino acids through their cell membranes when surrounded by an environment having a low concentration of such factors. Such loss of internal amino acids can have devastating effects. Again, as if in response to these needs of the osmolyte sensitive oocyte and cleavage stage embryo, the female reproductive tract typically has high levels of specific amino acids that are very similar to those found in the oocyte and cleavage stage embryo.

In view of the foregoing, an important object of the present invention is to further improve and enhance the culture of human reproductive cells in vitro. The invention is intended to promote the health and viability of the gametes, zygote and embryo at various stages of the IVF process, thereby improving the overall efficiency of the IVF process and increasing pregnancy rates.

In general, the present invention involves the application of separate media specifically formulated to meet the physiological needs of the gametes, zygote and/or developing embryo in various stages of their development, and to support the processes necessary to accomplish fertilization and embryonic development in vitro. The present invention also generally contemplates a sequential culture media system, in which the separate media utilized have integrated formulations, intended to minimize trauma to the reproductive cells as they are moved from one medium to another during the IVF process.

In one aspect of the present invention, an oocyte retrieval and handling medium is provided for use in the clinical procedure of retrieving the oocyte from the mother. The medium may be used for flushing, washing and holding the oocyte during the process of removing the oocyte from the mother's ovary, and for storing the oocyte for a period prior to fertilization. An optional use of the medium envisioned by the invention is with procedures where handling or manipulating the oocyte, zygote, or embryo is necessary, such as examination of the oocyte to determine whether fertilization has occurred, or examining the embryo to determine the progression of its development. The present invention includes use of an oocyte retrieval and handling medium comprised of water, ionic constituents, and a buffer. Preferably the buffer used in the medium is 4-Morpholinepropanesulfonic acid (MOPS) or N-2-hydroxyethylpiperazine-N'-2-ethane sulphonic acid (HEPES). In addition, the medium may be supplemented with the carbohydrates glucose, lactate and pyruvate. The medium may be supplemented with non-essential amino acids. An optional formulation of the medium, lacking calcium and magnesium, may be used in biospsy procedures. Another optional formulation of the medium includes antibiotics, such as penicillin and/or streptomycin, to destroy bacteria that might be introduced into the medium during the process of oocyte collection.

Another aspect of the present invention involves the provision and use of an oocyte maturation medium, for example, in circumstances where the oocyte is removed from the mother before it is mature. An example of a situation where application of this medium may be desired arises when it is necessary to treat the oocytes collected from the mother with hormones in vitro due to the mother's intolerance of such hormones. The invention contemplates holding the oocytes in the maturation medium for a period following collection of the oocytes, to promote development prior to fertilization. An optional use of the maturation medium in accordance with the invention is for collection, although the most cost effective approach will normally involve use of the retrieval and handling medium for initial flushing, washing, collection and storage, and then transfer to the maturation medium for an extended period prior to fertilization. The present invention contemplates use of a maturation medium comprised of water, ionic constituents, and a buffer. Preferably, the maturation medium is supplemented with the carbohydrates glucose, lactate and pyruvate. Specific formulations in accordance with the present invention may involve successive supplementation of the medium with one or more of the following: non-essential amino acids; essential amino acids; cysteamine; human serum albumin (HSA) and hyaluronate; one or more growth factors such as insulin transferin selenium (ITS), insulin-like growth factor (IGF), and epidermal growth factor (EGF); and hormones follicule stimulating hormone (FSH) and human chorionic gonadotrophin (hCG).

Another aspect of the invention involves the provision and use of a sperm preparation and fertilization medium. This medium may be applied to wash, prepare, and store sperm, to store the oocyte in the period prior to fertilization, and to serve as the medium in which the sperm and oocyte are placed together and fertilization occurs. The present invention contemplates use of a sperm preparation and fertilization medium that includes water, ionic constituents, and a buffer. Preferably, the medium contains an elevated concentration of sodium, as compared to the oocyte retrieval and handling medium, to promote sperm function and fertilization. In addition, the medium may be supplemented with an elevated phosphate concentration, as compared to the oocyte retrieval and handling medium. Even more preferably the medium is supplemented with the carbohydrates glucose, lactate and pyruvate. Specific formulations may involve supplementation of the medium with one or more of: bicarbonate; glutathione to promote sperm head decondensation; non-essential amino acids; HSA and hyaluronate; and antibiotics such as penicillin and streptomycin.

A further aspect of the invention relates to a medium for intracytoplasmic sperm injection (ICSI) and related methodology. The ICSI procedure may be necessary where there are obstacles to normal fertilization, such as a thickened zona pellucida on the oocyte hindering sperm head penetration. ICSI involves removal of the cumulus cells and injection of the sperm into the oocyte, ordinarily through a glass pipette. The invention contemplates placing sperm in the ICSI medium, capturing the sperm by drawing the medium containing sperm into the pipette, inserting the pipette containing medium and sperm into the oocyte, and, following insertion into the oocyte, transferring the medium containing sperm from the pipette into the oocyte. The ICSI medium used in the present invention includes the constituents water, ionic constituents and a buffer. Preferably, in the present invention the medium lacks phosphate. More preferably, the buffer used in the medium is MOPS or HEPES. Additionally, the medium may be supplemented with the carbohydrates lactate and pyruvate and the medium may be further supplemented with one or more of the non-essential acids most abundant in the oocyte: glutamine, glycine, proline, serine, and taurine. In one formulation, the ICSI medium used is supplemented with hyaluronate or polyvinylpyrolidone (PVP) to slow or immobilize the sperm so that they may be captured by pipette for the ICSI process. Further, an alternative formulation of the ICSI medium referred to as denuding medium used in the invention includes hyaluronidase, which is included in the portion of the medium used to denude the oocyte prior to the ICSI process.

Another aspect of the present invention involves the provision and use of a medium for supporting initial cell cleavage and embryonic development following fertilization, the medium herein referred to as G1.2. The invention contemplates washing the inseminated oocyte and zygote in the medium and placing the zygote in the medium for a period of about 48 hours to support cell cleavage and development through about the eight-cell stage. The present invention involves use of a medium that includes the constituents water, ionic constituents, and a buffer. Preferably, the medium is supplemented with the carbohydrates glucose, lactate, and pyruvate. The medium may also be supplemented with non-essential acids. Specific formulations in accordance with the invention may include one or more of the following supplements: EDTA; HSA; and hyaluronate. The form of glutamine used in the medium is preferably alanyl-glutamine, which is particularly stable and less prone to breakdown to the waste product ammonium, which is toxic to the developing embryo.

A further aspect of the invention involves the provision and use of a second medium for embryo development, herein referred to as G2.2. The invention contemplates placing the embryo in the G2.2 medium for a period of about 48 hours, preferably at or after the eight-cell stage, and continuing through the blastocyst stage of development and up to the point of embryo transfer. This medium is specifically adapted for and has as its preferred use support of the embryo from the eight-cell stage through the time at which implantation occurs, in tandem with the use of G1.2 for initial embryonic development. The invention involves a G2.2 medium that includes water, ionic constituents, and a buffer. Preferably the medium is supplemented with the carbohydrates glucose, lactate and pyruvate. More preferably, as compared to medium G1.2, medium G2.2 is supplemented with depressed levels of lactate and pyruvate, and elevated levels of glucose. Additionally, the medium may be supplemented with the non-essential amino acids, except taurine. Specific formulations in accordance with the present invention involve supplementing the medium with one or more of: essential amino acids, which stimulate development of the inner cell mass of the blastocyst; vitamins, which further facilitate the function of the blastocyst; HSA; and hyaluronate. An important aspect of the G2.2 medium, in all formulations, is the absence of EDTA.

Another aspect of the invention is the provision and use of an embryo transfer medium. The invention contemplates that this medium will be used as a carrier for the embryo when it is transferred back into the mother. The invention may involve the same formulations of the medium for embryo transfer as are used with medium G2.2. More preferably for embryo transfer, however, the formulation of G2.2 is supplemented with a higher concentration of hyaluronate, which supports implantation of the embryo in the mother's uterus.

A further aspect of the invention is the provision and use of a medium for cryopreservation of the embryo and/or oocyte. The invention contemplates that the embryo may be placed in the medium at either the one- to eight-cell stage or eight-cell to blastocyst stage, and then frozen and stored in the medium. The invention also contemplates that the medium may be used for cryopreservation of the oocyte. The cryopreservation medium contains ionic constituents, and a buffer. Preferably, it contains the MOPS or HEPES buffer. More preferably, it contains the carbohydrates lactate, pyruvate and glucose. Even more preferably, it contains HSA. Most preferably, the medium contains certain additives such as glycerol, ethylene glygol, DMSO, and/or sucrose.

According to a further aspect of the invention, different media are used for two different phases of the IVF process, such as oocyte collection and maturation, sperm preparation, fertilization, embryo development and/or embryo transfer. One associated process involves obtaining a gamete from a first medium and introducing the gamete into a second medium different from the first medium, wherein fertilization occurs in the second medium. The step of obtaining a gamete from a first medium may include extracting an oocyte from an oocyte collection medium or oocyte maturation medium as described above. Additionally or alternatively, the step of obtaining may involve extracting sperm from a sperm preparation and fertilization medium as described above which, in turn, may be different from the oocyte medium. The step of introducing the gamete into the second medium may involve introducing the sperm and/or oocyte into a fertilization medium, or injecting sperm into an oocyte contained in the second medium. The various media may have integrated formulations for minimizing trauma to the reproductive cells.

Another associated process in accordance with the present invention involves obtaining a zygote or embryo from a first medium wherein fertilization has occurred and introducing it into a second medium different from the first medium for a first growth phase. The first medium may be a fertilization medium as described above and the second medium may be the G1.2 medium as described above. The second medium may be used for supporting initial cell cleavage and embryonic development. The method may further involve transferring the resulting embryo from the second medium to a third medium for a second growth phase. The third medium may be a G2.2 medium as described above.

A further associated process in accordance with the present invention involves obtaining an embryo from a first medium and introducing the embryo into a second medium different from the first medium for transfer of the embryo into the mother for implantation. The first medium may be a G2.2 medium as described above and the second medium may be an embryo transfer medium as described above.

BRIEF DESCRIPTION OF THE DRAWING

For a more complete understanding of the present invention and further advantages thereof, reference is now made to the following detailed description taken in conjunction with the drawings, in which.

DETAILED DESCRIPTION OF THE INVENTION

Figure 1:
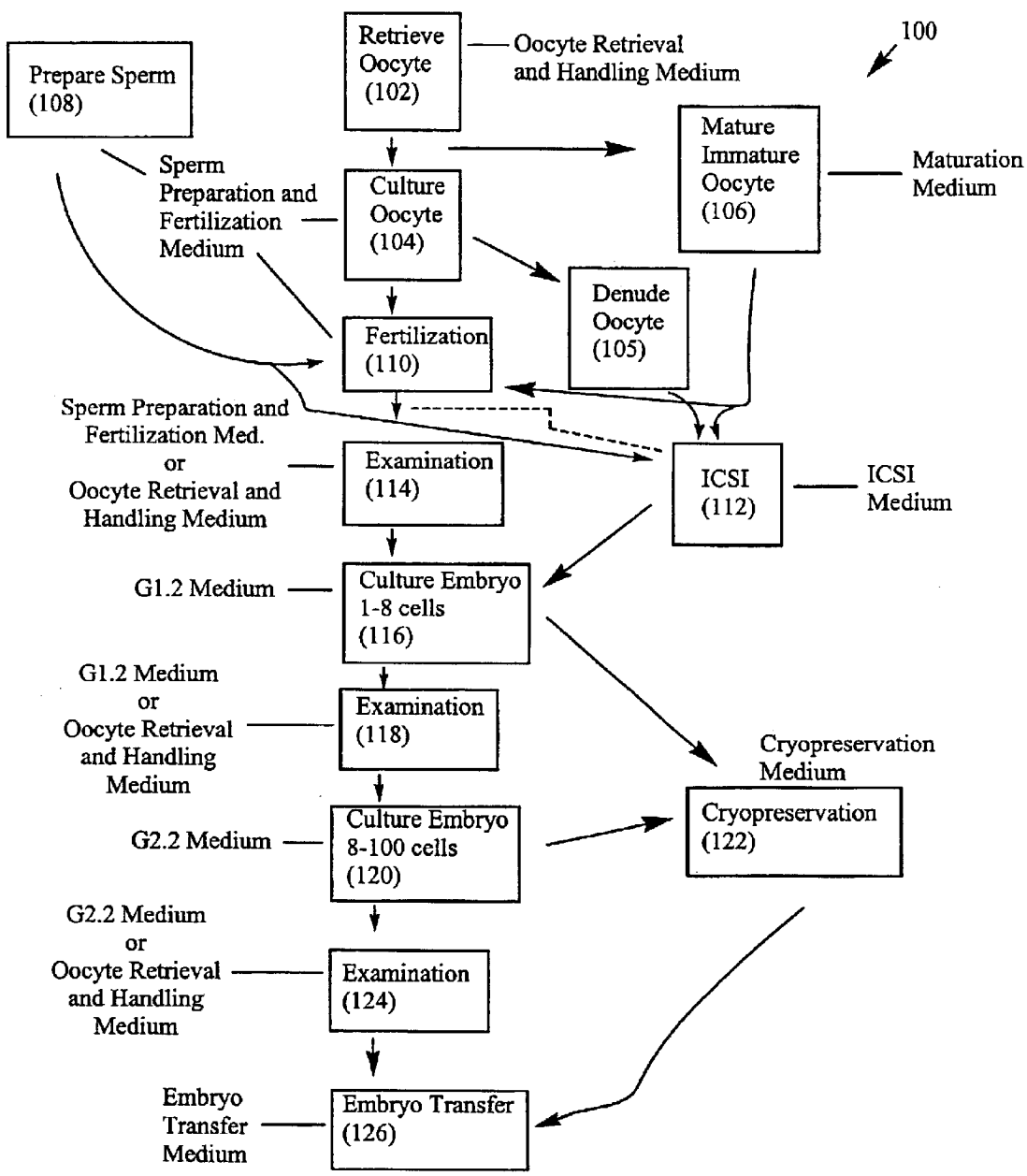
FIG. 1 is a flowchart illustrating an IVF process in accordance with the present invention.

The following description discloses the composition of various culture media in accordance with the present invention that are particularly adapted for use with IVF. Each of these media is specifically formulated to meet the physiological needs of the gametes, zygote and developing embryo at key points in the reproductive process. Also disclosed is a sequential culture media system. While each of the separate media could be used independently, the media also may be formulated together as a system, sharing a core group of ionic and non-essential amino acid constituents, with the objective of minimizing trauma to the oocyte, and the resulting zygote and embryo, as they are moved from one medium to another. The following description also discloses methods of using the media and the sequential culture media system in various clinical and laboratory procedures by which IVF is carried out, as well as methods of making the culture media.

A. Composition of the Sequential Culture Media

1. Oocyte Retrieval and Handling Medium

A preferred oocyte retrieval and handling medium is an aqueous solution comprised of the ionic components sodium, potassium, phosphate, magnesium, bicarbonate, and calcium, to maintain an osmotic environment that does not stress the oocyte, and a buffering system, preferably MOPS or HEPES, to maintain the pH of the medium within the physiological range of 7.3 to 7.4. The ionic components are included in the preferred amounts depicted in column A of Table 1, and may be included in amounts described in the ranges depicted in column B of Table 1.

TABLE 1

Composition of Oocyte Retrieval and Handling Medium*

| Component | | A<br>Most Preferred<br>Concentration | B<br>Preferred<br>Range |
|---|---|---|---|
| NaCl | | 90.08 | 75–105 |
| KCl | | 5.5 | 3.5–7.5 |
| NaH$_2$PO$_4$.2H$_2$O | | 0.25 | 0.05–1.5 |
| MgSO$_4$.7H$_2$O | | 1 | 0.2–4.0 |
| NaHCO$_3$ | | 5 | 2.0–10.0 |
| MOPS/HEPES | | 20 | 10.0–25.0 |
| CaCl$_2$.2H$_2$O | | 1.8 | 0.8–2.8 |
| Glucose | | 0.5 | 0.05–5.0 |
| NaLactate | (L-isomer) | 10.5 | 5.0–20.0 |
| NaPyruvate | | 0.32 | 0.1–1.0 |
| Alanine | (ala) | 0.1 | 0.01–0.5 |
| Asparate | (asp) | 0.1 | 0.01–0.5 |
| Asparagine | (asn) | 0.1 | 0.01–0.5 |
| Glutamate | (glu) | 0.1 | 0.01–0.5 |
| Alanyl - Glutamine | (ala - gln) | 0.5 | 0.01–2.0 |
| Glycine | (gly) | 0.1 | 0.01–0.5 |
| Proline | (pro) | 0.1 | 0.01–0.5 |
| Serine | (ser) | 0.1 | 0.01–0.5 |
| Taurine | (tau) | 0.1 | 0.01–10.0 |

*Concentrations are in millimoles unless otherwise indicated; the medium is aqueous.

It should be noted that Table 1 and the other tables presented in this section also describe the preferred form of the components used to make the respective culture media in practice. The MOPS buffer has not been used before in IVF procedures, and is preferred because it is not known to exhibit any toxic effects to reproductive cells and does not require maintenance of a $CO_2$ atmosphere above the medium. HEPES may also be utilized, although some research indicates a possible toxicity to reproductive cells. Table 1 depicts the preferred amount and ranges for the MOPS or HEPES buffer, although other buffering systems might be used. For example, a bicarbonate buffering system may be used because it is compatible with human reproductive cells. Such a system would not ordinarily be practical with oocyte collection, because it requires the maintenance of elevated levels of $CO_2$ in the atmosphere surrounding the medium, which is ordinarily accomplished by use of a gassing incubator system that maintains a 3%–10% $CO_2$ atmosphere. Oocyte collection is a clinical procedure, in which it is typically not possible to maintain an elevated $CO_2$ atmosphere. In some clinical environments, such as where a humidicrib is available, it may be possible to perform oocyte collection in an elevated $CO_2$ atmosphere, and a bicarbonate buffer accordingly may be used. In accordance with the present invention, any buffering system used preferably maintains its buffering qualities during exposure of the medium to the atmosphere, and as well is preferably compatible with and not toxic to human reproductive cells.

The oocyte retrieval and handling medium also includes the carbohydrates glucose, lactate, and pyruvate, at levels similar to those found in the female reproductive tract at the corresponding point of ovulation. The preferred amounts and ranges in which these are found in the medium are depicted in Table 1. In addition, the preferred medium contains Eagle's non-essential amino acids (i.e., those not required for the development of somatic cells in culture) alanine, aspartate, asparagine, glutamate, glycine, proline, serine, and taurine, plus glutamine in the form of alanyl-glutamine, at levels similar to those found in the female reproductive system and in the oocyte. The preferred amounts and ranges are depicted in Table 1. The inclusion of non-essential amino acids and alanyl-glutamine in the medium is important to preventing osmotic shock; a medium lacking these components may drain the oocyte of its internal pool of amino acids, resulting in considerable intracellular trauma. An optional formulation of the medium which may be used in biopsy procedures, omits calcium and magnesium. Another optional formulation of the medium may include one or more antibiotics, such as penicillin and streptomycin, to destroy any bacteria that might be present around the oocyte or that might be introduced through the clinical procedure of oocyte removal.

2. Oocyte Maturation Medium

The oocyte maturation medium is adapted for use with immature oocytes. Oocyte maturation is typically used with mothers who are unable to withstand the hormonal treatment ordinarily employed in IVF. Oocyte maturation generally involves treating the immature oocytes in vitro with the hormones follicle stimulating hormone (FSH) and human chorionic gonadotrophin (hCG) rather than injecting these hormones into the mother. The preferred medium is an aqueous solution that contains ionic constituents similar to those used in the oocyte retrieval and handling medium, at similar concentrations, although the magnesium level is increased and the calcium level decreased to maintain a 2:1 magnesium to calcium concentration. A buffer is included in the preferred medium to maintain a physiological pH. Because oocyte maturation ordinarily occurs in an incubator or isolette in which an elevated $CO_2$ atmosphere can be maintained, a bicarbonate buffering system is preferred. Other buffers may be used, provided they are compatible with the oocyte and other components of the medium. Table 2 provides the most preferred amounts of each of these components, as well as the preferred ranges of these components.

TABLE 2

Composition of Oocyte Maturation Medium*

| Component | A<br>Most Preferred<br>Concentration | B<br>Preferred<br>Range |
|---|---|---|
| NaCl | 90.08 | 80.0–100 |
| KCl | 5.5 | 3.5–7.5 |
| $NaH_2PO_4 \cdot 2H_2O$ | 0.25 | 0.05–1.5 |
| $MgSO_4 \cdot 7H_2O$ | 2 | 0.2–4.0 |
| $NaHCO_3$ | 25 | 15–30.0 |
| $CaCl_2 \cdot 2H_2O$ | 1 | 0.8–2.8 |
| Glucose | 3.15 | 0.5–5.5 |
| NaLactate (L-isomer) | 5.87 | 2.0–20.0 |
| NaPyruvate | 0.1 | 0.01–1.0 |
| Alanine | 0.1 | 0.01–0.5 |
| Asparate | 0.1 | 0.01–0.5 |
| Asparagine | 0.1 | 0.01–0.5 |
| Glutamate | 0.1 | 0.01–0.5 |
| Alanyl - Glutamine | 1 | 0.01–2.0 |
| Glycine | 0.1 | 0.01–0.5 |
| Proline | 0.1 | 0.01–0.5 |
| Serine | 0.1 | 0.01–0.5 |
| Cysteamine | 0.5 | 0.1–2.0 |
| L-Arginine-HCl | 0.6 | 0.1–1.2 |
| L-Cystine 2HCl | 0.1 | 0.05–0.25 |
| L-Histidine-HCl-H2O | 0.2 | 0.1–0.4 |
| L-Isoleucine | 0.4 | 0.1–0.8 |
| L-Leucine | 0.4 | 0.1–0.8 |
| L-Lysine-HCl | 0.4 | 0.1–0.8 |
| L-Methionine | 0.1 | 0.05–0.25 |
| L-Phenylalanine | 0.2 | 0.1–0.4 |
| L-Threonine | 0.4 | 0.1–0.8 |
| L-Tryptophan | 0.5 | 0.1–0.9 |
| L-Tyrosine 2Na | 0.2 | 0.1–0.4 |
| L-Valine | 0.4 | 0.1–0.8 |
| D-Ca Pantothenate | 0.002 | 0.001–0.004 |
| Choline Chloride | 0.007 | 0.003–0.01 |
| Folic Acid | 0.0023 | 0.001–0.0045 |
| i-Inositol | 0.0111 | 0.005–0.02 |
| Niacinamide | 0.0082 | 0.004–0.016 |
| Pyridoxal HCl | 0.0049 | 0.002–0.01 |
| Riboflavin | 0.0003 | 0.0001–0.0006 |
| Thiamine HCl | 0.003 | 0.001–0.006 |
| HSA | 5 mg/ml | 1–10.0 |
| Hyaluronate | 0.25 mg/ml | 0.05–0.5 |
| ITS | 10 ng/ml | 1–100 |
| IGF-I | 100 ng/ml | 10–1000 |
| EGF | 100 ng/ml | 10–1000 |
| FSH | 0.1 U/ml | 0.01–10 |
| hCG | 0.1 U/ml | 0.01–10 |

*Concentrations are in millimoles, unless otherwise indicated; the medium is aqueous.

The carbohydrates glucose, lactate and pyruvate are also included in the preferred maturation medium. Because of the presence and importance of cumulus cells that surround the developing oocyte, the glucose, lactate and pyruvate levels are adapted to the needs of the cumulus cells. Non-essential amino acids are preferably included in the medium to provide nutrients and avoid subjecting the oocyte to osmotic stress. Essential amino acids and vitamins may also be included to provide nutrients to the cumulus cells. The medium also contains HSA and hyaluronate, which act as a source of macromolecules. Insulin transferin selenium (ITS), insulin-like growth factor (IGF), and epidermal growth factor (EGF) are included to support the function of cumulus cells, which, in turn, nourish and stimulate the oocyte. FSH and hCG are added to stimulate the cumulus and oocyte to undergo changes associated in vivo with ovulation. It should be noted that, when the maturation medium is prepared, ITS, IGF, EGF and FSH and hCG are preferably the last-added ingredients. The preferred amounts and ranges of these components are found in Table 2.

3. Sperm Preparation and Fertilization Medium

Current methods of in vitro fertilization employ the same medium for sperm preparation and fertilization as is used for embryo development. No attempt has been made to develop a separate medium for preparation of sperm that is also suitable for storage and support of the oocyte, for promoting the process of fertilization, and for supporting the zygotes formed when fertilization occurs. In many laboratories, the fertilization process is allowed to take place over an extended period which ranges from two to three hours to up to about sixteen (16) to eighteen (18) hours. During this time, the oocyte, sperm, and zygotes produced have significant nutritional needs. In addition, sperm function and fertilization tend to be encouraged when the surrounding fluid contains certain constituents. The sperm preparation and fertilization medium of the present invention is formulated to meet these concerns.

A preferred sperm preparation and fertilization medium in accordance with this invention has virtually the same composition of ions and non-essential amino acids as the oocyte retrieval and handling medium. The fact that these media share a similar ionic and amino acid composition minimizes the stress experienced by the oocyte when it is removed from the retrieval and handling medium and placed in sperm preparation medium. Table 3 sets out the preferred amounts and ranges of the ionic and non-essential acid components.

TABLE 3

Composition of Sperm Preparation and Fertilization Medium*

| Component | A<br>Most Preferred<br>Concentration | B<br>Preferred<br>Range |
|---|---|---|
| NaCl | 100 | 75–100 |
| KCl | 5.5 | 3.5–7.5 |
| $NaH_2PO4 \cdot 2H2O$ | 0.5 | 0.05–1.5 |
| $MgSO4 \cdot 7H2O$ | 1 | 0.2–4.0 |
| Glucose | 3.15 | 0.5–5.6 |
| NaLactate (L-isomer) | 5 | 2.0–20 |
| NaPyruvate | 0.32 | 0.1–0.5 |
| NaHCO3 | 25 | 15–30 |
| $CaCl2 \cdot 2H2O$ | 1.8 | 0.8–2.8 |
| Glutathione | 1.0 mg/ml | 0.5–5.0 |
| Alanine | 0.1 | 0.01–0.5 |
| Asparate | 0.1 | 0.01–0.5 |
| Asparagine | 0.1 | 0.01–0.5 |
| Glutamate | 0.1 | 0.01–0.5 |
| Glycine | 0.1 | 0.01–0.5 |
| Proline | 0.1 | 0.01–0.5 |
| Serine | 0.1 | 0.01–0.5 |
| Taurine | 0.1 | 0.01–10.0 |
| HSA | 5 mg/ml | 1.0–10.0 |
| Hyaluronate | 0.1 mg/ml | 0.02–0.5 |
| Penicillin | 0.06 mg/ml | 0.01–.10 |
| Streptomycin | 0.05 mg/ml | 0.01–.10 |

*Concentrations are in millimoles unless otherwise indicated; the medium is aqueous.

As will be seen, the sperm preparation medium contains sodium at a higher concentration than the level found in the oocyte retrieval and handling medium. This elevated concentration of sodium promotes sperm function and fertilization, without causing undue osmotic stress to the oocyte. There is also a higher concentration of phosphate, as compared to the oocyte retrieval and handling medium. The glucose concentration of the sperm preparation and fertilization medium is elevated over that of the oocyte retrieval and handling medium, because glucose is the primary nutrient for sperm and cumulus cells around the egg. The lactate concentration of the present medium is lower than that found in the oocyte retrieval and handling medium, to compensate for the tendency of sperm cells and cumulus cells to give off lactic acid as a waste product. A buffering system is used to maintain the physiological pH, and because sperm preparation and fertilization largely occur within an incubator that can maintain an elevated $CO_2$ atmosphere, a bicarbonate buffer is preferred. Glutathione (not present in the oocyte retrieval and handling medium) is included, to assist in the process of sperm head decondensation. Alanyl-glutamine (present in the oocyte retrieval and handling medium) is omitted from the present medium because it can impair sperm function and reduce fertilization. The same is true of the chelating agent EDTA, which (as will be discussed later) is present in the embryo development media. HSA, the most abundant macromolecule in the Fallopian tube and uterus, is included to support sperm and embryo function. Hyaluronate, which promotes sperm motility, and works in tandem with HSA, is also included. Because sperm tends to contain high levels of bacteria, one or more antibiotic substances are also included. Penicillin, streptomycin, and/or gentamycin are preferred antibiotics. Table 3 sets out the preferred amounts and ranges for these various components.

4. The ICSI Medium

In circumstances where it is desired to accomplish fertilization by other than natural interaction of sperm and oocyte, such as where the sperm is unable to fertilize the oocyte due to a thickened zona pellucida surrounding the oocyte, or where the sperm is from a male-factor patient, the sperm may be transported into the oocyte by a technique called intracytoplasmic sperm injection (ICSI). When the ICSI technique is used, the cumulus cells are removed from the oocyte, and sperm is injected into the oocyte's interior using a glass pipette. The present invention contemplates use of a single medium to bathe the oocyte and also to serve as a carrier for the sperm as it is transported by injection into the oocyte. The medium, accordingly, is preferably highly compatible with the interior and exterior of the oocyte. The ionic constituents in the preferred medium are similar to those found in the oocyte retrieval and handling medium, except that phosphate is omitted, to avoid metabolic and homeostatic stress, and the magnesium-to-calcium ratio is 2:1. This ratio of magnesium to calcium is felt to be highly beneficial to the oocyte. Because ICSI is a clinical procedure performed outside the incubator, a buffering system that is effective in a normal atmosphere is used. MOPS and HEPES are accordingly preferred buffers for this medium. Because the cumulus cells have been removed from the oocyte, and the sperm is at the conclusion of its independent life, glucose, the main energy source for cumulus cells and sperm (but not the oocyte) is omitted from the medium. Pyruvate and lactate levels are increased, as these are a primary energy source for the oocyte. Only the non-essential amino acids most abundant in the oocyte—glycine, proline, serine and taurine—and glutamine (in the stable form alanyl-glutamine) are retained in the medium to avoid osmotic and pH stress and to nourish the oocyte. Preferably, the ICSI medium also includes hyaluronate or polyvinylpyrollidone (PVP), to immobilize or slow the sperm so that they may be captured in the ICSI pipette. Table 4 sets out the preferred amounts and the ranges of these components in the ICSI medium. Moreover, an alternative formulation of the ICSI medium includes hyaluronidase, which alternative formulation is used to pretreat the oocyte, to break down the hyaluronate gel holding the cumulus cells around the oocyte. This medium is referred to above as denuding medium, and lacks hyaluronate and PVP but includes hyaluronidase. The composition of the denuding medium includes the constituents of the ICSI medium (except hyaluronate and PVP) in the preferred amounts and ranges shown in Table 4 plus hyaluronidase in a preferred about of 40 IU/ml and a preferred range of Oct-80. Optionally, HSA may be included in the denuding medium in the preferred amount of 5 mM and the preferred range of 1.0–10 mM.

TABLE 4

Composition of Medium ICSI*

| Component | A<br>Most Preferred<br>Concentration | B<br>Preferred<br>Range |
|---|---|---|
| NaCl | 90.08 | 75.0–105 |
| KCl | 5.5 | 3.5–7.5 |
| $MgSO_4.7H_2O$ | 2 | 0.4–4 |
| $NaHCO_3$ | 5 | 2.0–10 |
| MOPS/HEPES | 20 | 10–25.0 |
| $CaCl_2.2H_2O$ | 1 | 0.5–2.0 |
| NaLactate (L-isomer) | 10.5 | 5.0–20 |
| NaPyruvate | 0.32 | 0.1–1.0 |
| Alanyl–Glutamine | 0.5 | 0.1–2.0 |
| Glycine | 0.5 | 0.1–2.0 |
| Proline | 0.1 | 0.05–2.0 |
| Serine | 0.1 | 0.05–2.0 |
| Taurine | 0.1 | 0.05–5.0 |
| HSA | 5 mg/ml | 1–10.0 |
| Hyaluronate | 0.1 mg/ml | 0.02–0.5 |
| PVP | 10% | 1–20% |

*Concentrations are in millimoles unless otherwise indicated; the medium is aqueous.

5. Embryonic Development Medium G1.2.

The present invention includes an embryonic development medium G1.2. The preferred application of this medium is to support development of the early one-to-eight cell embryo. As depicted in Table 5, the preferred medium has a backbone of ionic constituents and non-essential amino acids that is similar to that found in the oocyte retrieval and handling medium. Unlike the oocyte retrieval and handling medium, the G1.2 medium contains the component EDTA, which supports embryonic development and is believed to bind and disable toxins that might have a deleterious effect on the early embryo, and which also suppresses glycolysis. In addition, this medium includes HSA and hyaluronate, in concentrations that are thought to support early embryonic development.

The preferred formulation of medium G1.2 differs from the previously published medium G1 in several important respects. First, research has shown that an elevated phosphate concentration may not provide optimal conditions for growth of the developing embryo. Accordingly, the phosphate concentration has been decreased. Second, hyaluronate has been added to work in tandem with HSA. Third, alanyl-glutamine has been substituted for glutamine. A significant problem for embryo culture with amino acids is the natural decomposition of amino acids to ammonium, which decomposition is accelerated at higher temperatures such as the physiological temperature (37 degrees Celsius) used in IVF procedures. Ammonium can be toxic to embryos. Moreover, glutamine is especially prone to decomposition to ammonium within solution. Since embryos are generally cultured in medium G1 or G1.2 for an extended period of up to about 48 hours, a significant quantity of ammonium can develop in the medium and be a significant inhibitor to embryo development. Accordingly, the use of alanyl-glutamine provides substantial advantages; it is a particularly stable form of glutamine and is not prone to breaking down in solution. Also, the concentration of alanyl-glutamine in G1.2 has been reduced to 0.5 mM. These three modifications make G1.2 a significantly improved medium for early embryonic development over medium G1. The most preferred amounts and preferred ranges of the components of medium G1.2 are depicted in Table 5.

TABLE 5

Composition of Medium G 1.2*

| Component | A Most Preferred Concentration | B Preferred Range |
|---|---|---|
| NaCl | 90.08 | 80.0–100 |
| KCl | 5.5 | 3.5–7.5 |
| NaH$_2$PO$_4$.2H$_2$O | 0.25 | 0.05–1.5 |
| MgSO$_4$.7H$_2$O | 1 | 0.2–2.0 |
| NaHCO$_3$ | 25 | 15.0–30 |
| CaCl$_2$.2H$_2$O | 1.8 | 0.8–2.8 |
| Glucose | 0.5 | 0.05–5.0 |
| NaLactate (L-isomer) | 10.5 | 5.0–20. |
| NaPyruvate | 0.32 | 0.1–1.0 |
| Alanine | 0.1 | 0.01–0.5 |
| Asparate | 0.1 | 0.01–0.5 |
| Asparagine | 0.1 | 0.01–0.5 |
| Glutamate | 0.1 | 0.01–0.5 |
| Alanyl - Glutamine | 0.5 | 0.1–1.0 |
| Glycine | 0.1 | 0.01–0.5 |
| Proline | 0.1 | 0.01–0.5 |
| Serine | 0.1 | 0.01–0.5 |
| Taurine | 0.1 | 0.01–10.0 |
| EDTA | 0.01 | 0.005–0.20 |
| HSA | 5 mg/ml | 1–10.0 |
| Hyaluronate | 0.1 mg/ml | 0.02–0.5 |

*Concentrations are in millimoles unless otherwise indicated; the medium is aqueous.

6. Embryonic Development Medium G2.2

Medium G2.2 is also formulated to support embryonic development. Its preferred use is with embryos from the eight-cell to the blastocyst stage (around 100 cells) to around one-hundred cell stage. The backbone of ionic constituents and non-essential amino acids preferably found in medium G2.2 is essentially the same as used with medium G1.2, except that the concentration of alanyl-glutamine has been increased. This reduces the risk of subjecting the embryo to osmotic stress as it is moved from medium G1.2 to medium G2.2. Taurine is omitted because its benefits to the embryo appear to be confined to the period prior to compaction. Glucose, lactate and pyruvate are included as carbohydrates, except that the concentration of glucose is increased, while lactate and pyruvate are decreased, as compared to medium G1.2. This modification in carbohydrate levels is in response to the increasing ability of the developing embryo to metabolize glucose as an energy source, and reflects also the observed composition of the female reproductive tract. Eagle's essential amino acids are included in medium G2.2 because they are necessary to stimulate the growth of the inner-cell mass of the blastocyst. Vitamins are added as a group because in animal studies they tend to facilitate the function of the blastocyst, including fluid accumulation in the cavity of the blastocyst. Importantly, this medium lacks EDTA. The preferred amounts and ranges of the components of medium G2.2 are depicted in Table 6.

TABLE 6

Composition of Medium G 2.2*

| Component | A Most Preferred Concentration | B Preferred Range |
|---|---|---|
| NaCl | 90.08 | 80.0–100 |
| KCl | 5.5 | 3.5–7.5 |

TABLE 6-continued

Composition of Medium G 2.2*

| Component | A Most Preferred Concentration | B Preferred Range |
|---|---|---|
| NaH2PO4.2H2O | 0.25 | 0.05–1.5 |
| MgSO4.7H2O | 1 | 0.2–4.0 |
| NaHCO3 | 25 | 15–30.0 |
| CaCl2.2H2O | 1.8 | 0.8–2.8 |
| Glucose | 3.15 | 0.5–5.5 |
| NaLactate (L-isomer) | 5.87 | 2.0–20.0 |
| NaPyruvate | 0.1 | 0.01–1.0 |
| Alanine | 0.1 | 0.01–0.5 |
| Asparate | 0.1 | 0.01–0.5 |
| Asparagine | 0.1 | 0.01–0.5 |
| Glutamate | 0.1 | 0.01–0.5 |
| Alanyl - Glutamine | 1 | 0.01–2.0 |
| Glycine | 0.1 | 0.01–0.5 |
| Proline | 0.1 | 0.01–0.5 |
| Serine | 0.1 | 0.01–0.5 |
| L-Arginine-HCl | 0.6 | 0.1–1.2 |
| L-Cystine 2HCl | 0.1 | 0.05–0.25 |
| L-Histidine-HCl-H2O | 0.2 | 0.1–0.4 |
| L-Isoleucine | 0.4 | 0.1–0.8 |
| L-Leucine | 0.4 | 0.1–0.8 |
| L-Lysine-HCl | 0.4 | 0.1–0.8 |
| L-Methionine | 0.1 | 0.05–0.25 |
| L-Phenylalanine | 0.2 | 0.1–0.4 |
| L-Threonine | 0.4 | 0.1–0.8 |
| L-Tryptophan | 0.5 | 0.1–0.9 |
| L-Tyrosine 2Na | 0.2 | 0.1–0.4 |
| L-Valine | 0.4 | 0.1–0.8 |
| D-Ca Pantothenate | 0.002 | 0.001–0.004 |
| Choline Chloride | 0.007 | 0.003–0.01 |
| Folic Acid | 0.0023 | 0.001–0.0045 |
| i-Inositol | 0.0111 | 0.005–0.02 |
| Niacinamide | 0.0082 | 0.004–0.016 |
| Pyridoxal HCl | 0.0049 | 0.002–0.01 |
| Riboflavin | 0.0003 | 0.0001–0.0006 |
| Thiamine HCl | 0.003 | 0.001–0.006 |
| HSA | 5 mg/ml | 1–10.0 |
| Hyaluronate | 0.1 mg/ml | 0.02–0.5 |

*Concentrations are in millimoles unless otherwise indicated; the medium is aqueous.

7. Embryo Transfer Medium

The preferred embryo transfer medium contains the same formulation of constituents as medium G2.2 except that a much higher concentration of hyaluronate is included. In the human reproductive system, research indicates that there is a receptor on the embryo for hyaluronate and that there is also a receptor for hyaluronate on the endometrium of the mother. Hyaluronate is thought to act like a biological glue that assists the embryo in binding to the endometrium and, accordingly, supports implantation. The preferred amount and ranges of the constituents of the embryo transfer medium are depicted in Table 7.

TABLE 7

Composition of Embryo Transfer Medium*

| Component | A Most Preferred Concentration | B Preferred Range |
|---|---|---|
| NaCl | 90.08 | 80.0–100 |
| KCl | 5.5 | 3.5–7.5 |
| NaH2PO4.2H2O | 0.25 | 0.05–1.5 |
| MgSO4.7H2O | 1 | 0.2–4.0 |
| NaHCO3 | 25 | 15–30.0 |
| CaCl2.2H2O | 1.8 | 0.8–2.8 |

TABLE 7-continued

Composition of Embryo Transfer Medium*

| Component | A<br>Most Preferred<br>Concentration | B<br>Preferred<br>Range |
|---|---|---|
| Glucose | 3.15 | 0.5–5.5 |
| NaLactate (L-isomer) | 5.87 | 2.0–20.0 |
| NaPyruvate | 0.1 | 0.01–1.0 |
| Alanine | 0.1 | 0.01–0.5 |
| Asparate | 0.1 | 0.01–0.5 |
| Asparagine | 0.1 | 0.01–0.5 |
| Glutamate | 0.1 | 0.01–0.5 |
| Alanyl - Glutamine | 1 | 0.01–2.0 |
| Glycine | 0.1 | 0.01–0.5 |
| Proline | 0.1 | 0.01–0.5 |
| Serine | 0.1 | 0.01–0.5 |
| L-Arginine-HCl | 0.6 | 0.1–1.2 |
| L-Cystine 2HCl | 0.1 | 0.05–0.25 |
| L-Histidine-HCl-H2O | 0.2 | 0.1–0.4 |
| L-Isoleucine | 0.4 | 0.1–0.8 |
| L-Leucine | 0.4 | 0.1–0.8 |
| L-Lysine-HCl | 0.4 | 0.1–0.8 |
| L-Methionine | 0.1 | 0.05–0.25 |
| L-Phenylalanine | 0.2 | 0.1–0.4 |
| L-Threonine | 0.4 | 0.1–0.8 |
| L-Tryptophan | 0.5 | 0.1–0.9 |
| L-Tyrosine 2Na | 0.2 | 0.1–0.4 |
| L-Valine | 0.4 | 0.1–0.8 |
| D-Ca Pantothenate | 0.002 | 0.001–0.004 |
| Choline Chloride | 0.007 | 0.003–0.01 |
| Folic Acid | 0.0023 | 0.001–0.0045 |
| i-Inositol | 0.0111 | 0.005–0.02 |
| Niacinamide | 0.0082 | 0.004–0.016 |
| Pyridoxal HCl | 0.0049 | 0.002–0.01 |
| Riboflavin | 0.0003 | 0.0001–0.0006 |
| Thiamine HCl | 0.003 | 0.001–0.006 |
| Hyaluronate | 0.25 mg/ml | 0.05–1.0 |

*Concentrations are in millimoles, unless otherwise indicated; the medium is aqueous.

8. Cryopreservation Medium

The present invention involves a separate medium to be used in cryopreservation of the oocyte and embryo. The preferred formulation to be used includes ionic constituents and a buffer, preferably MOPS or HEPES, as well as the carbohydrates lactate, pyruvate and glucose. Optionally, HSA may be included. In addition, the medium may include certain additives, glycerol, ethylene glycol, DMSO, propanedial, and/or sucrose. The preferred amounts and ranges of the constituents of the cryopreservation medium are depicted in Table 8.

TABLE 8

Composition of Cryopreservation Medium*

| Component | A<br>Most Preferred<br>Concentration | B<br>Preferred Range |
|---|---|---|
| NaCl | 90.08 | 75.0–105 |
| KCl | 5.5 | 3.5–7.5 |
| MgSO$_4$, 7H$_2$O | 2 | 0.4–4 |
| Na2PO4.2H2O | 0.25 | 0.1–1.5 |
| NaHCO$_3$ | 5 | 2.0–10 |
| MOPS/HEPES | 20 | 10–25.0 |
| CaCl$_2$.2H$_2$O | 1 | 0.5–2.0 |
| NaLactate (L-isomer) | 5.87 | 2.0–20 |
| NaPyruvate | 0.32 | 0.1–1.0 |
| Glucose | 1 | 0.5–5.5 |
| HSA | 5 mg/ml | 1.0–10 |

Additives
Glycerol and/or ethylene glycol and/or DMSO and/or pkropanediol and/or sucrose Range for all except sucrdose is 2 to 20%; range for sucrose is 0.1 to 1M Concentrations are in millimeters unless otherwise indicated; the medium is aqueous B. Sequential Culture Media Process Instead of immersing human reproductive cells in a single culture medium throughout the various procedures used in IVF, the present invention involves a process by which the reproductive cells may be moved through a sequence of distinct culture media as the various IVF procedures are carried out. In one aspect of the invention, the culture media are specifically formulated to provide a physical environment similar to that found within the female reproductive tract and conducive to growth and development of human reproductive cells during various stages of the IVF process. In a further aspect of the invention, the specifically formulated culture media can be applied to support the reproductive cells in one or more of the following procedures: oocyte retrieval and handling; oocyte maturation; ordinary fertilization; oocyte, zygote and embryo examination and biopsy; embryonic development to the eight-cell stage; embryonic development to the blastocyst stage; embryo transfer; and cryopreservation. Most preferably, the media will be applied sequentially during each of the applicable stages of the IVF process to which the media have been adapted. It should be noted that there is significant variation among clinics and laboratories as to equipment and specific procedures used to accomplish each of the principal steps in the IVF process. The present invention contemplates that the sequential media and process described herein may be utilized and/or readily adapted for use with the wide variety of equipment and procedures employed in IVF practice. What follows is a more detailed discussion of exemplary applications of the media during IVF and related methodology:

1. Oocyte Retrieval and Handling; Embryo Handling

Referring to FIG. 1, an initial procedure in the illustrated IVF process 100 is oocyte removal or retrieval (102) from the mother's ovary. This is typically performed vaginally using a fine needle attached to and guided by a transvaginal ultrasound probe. The needle is ordinarily connected to fine Teflon tubing and thence to an aspiration regulator controlled by a vacuum regulator. The aspirate is collected in test tubes or other appropriate vessels, containing medium. The medium may be used to preliminarily wash the needle and tubing, and other equipment used in the procedure. In some clinical settings, the medium may also be used with a specially adapted needle to flush the follicle and aid in removal of the oocyte. The medium, equipment used, and aspirate are maintained, so far as possible, at 37 degrees Celsius. If a bicarbonate buffer system is used in the medium, the procedure ordinarily is carried out in a gassed humidicrib or isolette which maintains a 3%–10% $CO_2$ atmosphere. In the absence of such atmospheric controls, the medium must contain a MOPS or HEPES buffering system.

The illustrated process 100 present invention contemplates that the oocyte retrieval and handling medium may be used in each phase of the retrieval process. The process of using the oocyte retrieval and handling medium may involve washing any equipment that may come into contact with the oocyte during removal from the ovary, and that may be used to aspirate, flush and/or wash the oocyte during the removal and collection process. Following removal from the ovary, the oocyte may be washed with medium. Optionally, the oocyte may be stored in the medium for a period.

In addition, it is contemplated that the medium may be used during other clinical or laboratory procedures where the oocyte is manipulated or handled, and also in procedures where the embryo is manipulated or handled, especially where these occur outside the isolette. Examples would include examination of the oocyte following retrieval from the mother, examination of the oocyte following the fertilization step, and examination of the embryo to determine whether it has developed the eight-cell stage. In each of these examples, the oocyte/embryo would be bathed in the medium as it is withdrawn by pipette from the culture dish or test tube, and would remain immersed in the medium while examined under a microscope or with other equipment. The illustrated implementation of the invention also contemplates that an alternative formulation of this medium, which is calcium and magnesium free, may be used during biopsy procedures.

2. Oocyte Maturation

In the event the collected oocytes are immature, the illustrated process 100 envisions that a second medium may be used to support and promote development of the oocyte during maturation (106). The oocyte maturation medium would ordinarily be used to treat and mature the oocyte following a collection procedure, in which the oocyte is retrieved from the ovary using oocyte retrieval and handling medium. The retrieval and handling medium and maturation medium have a very similar backbone of ionic constituents and amino acids and glutamine, such that as the oocyte is moved from one medium to another it experiences minimal ionic shock. The illustrated process 100 includes immersing the oocyte and surrounding cumulus cells in the maturation medium for a period of about 30–48 hours, or until the oocyte is mature. The illustrated process 100 then contemplates removing the oocyte from the maturation medium and immersing it in either sperm preparation and fertilization medium or ICSI medium for purposes of fertilization.

In accordance with the invention, the oocyte maturation medium may be applied to the oocyte retrieval process (102), in place of the oocyte retrieval and handling medium described herein. Additionally, a conventional culture medium, such as Ham's F-10 or medium TCM-199 with or without a HEPES buffer, may be employed for immature oocyte retrieval and handling, before immersion of the oocyte in the maturation medium of the present invention. Once maturation is complete, the oocyte will be immersed in a medium for ordinary IVF fertilization procedure (110), or will be immersed in an ICSI medium in preparation for assisted insemination through an ICSI procedure (112).

3. Sperm Preparation and Fertilization

The illustrated process 100 contemplates that the collected oocytes will ordinarily be washed and immersed in, and allowed a period of pre-incubation culture within, a first portion of the sperm preparation and fertilization medium. This period of pre-incubation culture (104) may last up to about six (6) hours. Oocytes permitted a period of pre-incubation culture typically have higher fertilization rates.

The process 100 also contemplates that the sperm may be separately washed and stored in a second portion of the sperm preparation and fertilization medium to purge it of bacteria and any other contaminants that may be present. Sperm preparation (108) may involve dilution of semen with the medium, centrifugation, and resuspension of the concentrated sperm in a new portion of medium. In the "swim up" method of sperm preparation, the medium containing sperm is centrifuged, the medium is drained off, and a new portion of medium is poured over the spun-down sperm pellet. The sperm is given a period to "swim up" into the fresh medium. That layer of fresh medium, containing the more motile sperm, is then poured off and centrifuged, and the process is repeated. In another aspect of the invention, the sperm preparation and fertilization medium may be used in one or more gradient separation procedures, such as the Percoll procedure. The present invention envisions that the sperm preparation and fertilization medium may be used as the medium in any of the sperm preparation procedures that may be used for IVF.

Once the sperm is prepared (108), the sperm is then examined and counted while in medium, and a desired quantity is added to the portion of medium which contains the oocyte. The sperm and oocyte are permitted to remain together in the medium for a period of up to several hours, and, in some laboratories, for a much longer period, as long as about sixteen (16) to eighteen (18) hours. The invention further contemplates that, following a period of immersion in the medium with sperm, the oocytes will be removed and examined (114) to determine whether fertilization (110) has occurred. When removed for examination, the oocytes will continue to be bathed in the sperm preparation and fertilization medium if the examination can be conducted in an isolette. If not, then, as noted above, the oocyte retrieval and handling medium may be used for handling and examination of the oocytes.

4. Fertilization by Direct Injection of Sperm into the Oocyte (ICSI Technique)

In the ICSI process (112), sperm may be directly injected into the cytoplasm of the oocyte through a very fine pipette or needle. The process 100 contemplates washing the sperm with a portion of the ICSI medium containing hyaluronate and/or PVP, and then placing the sperm in the medium. The process 100 further involves drawing a microvolume of the medium containing sperm into the pipette and then injecting the medium and sperm into the interior of the oocyte.

The illustrated process 100 further contemplates that the oocyte may be bathed in another portion of the ICSI medium during the ICSI process. An alternative formulation of the ICSI medium may be used, supplemented with hyaluronidase, for denuding pretreatment (105) of the oocyte prior to the ICSI process. Pretreatment involves immersing the oocyte in the ICSI medium supplemented with hyaluronidase for a period until the oocyte becomes denuded of all or most of its surrounding cumulus cells. Following pretreatment, the oocyte is injected with sperm carried in a separate portion of medium, using an ICSI pipette, as provided above.

After the ICSI injection process (112) is complete, it may be necessary to examine (114) the oocyte to evaluate whether fertilization has been effective and the oocyte is intact and healthy. Examination may occur in the ICSI medium bathing the oocyte, or may occur in the oocyte retrieval and handling medium as described above.

5. Embryonic Development to Eight-Cell Stage

Medium G1.2 is applied to the early embryo, following formation of the zygote. After the zygote is identified, it is washed with medium G1.2, and then immersed in G1.2 medium for a culturing period (116) of up to about forty-eight hours. During this time the embryo undergoes development from the one-cell to around the eight-cell stage, and is removed at about the eight-cell stage. Examination (118) of the embryo may occur in the G1.2 medium, or in the oocyte retrieval and handling medium, as described above.

6. Embryonic Development to Blastocyst Stage

The illustrated process 100 contemplates that medium G2.2 will be used to culture (120) the developing embryo to the blastocyst stage, preferably from about the eight-cell stage to about the one-hundred-cell stage. The process 100 also contemplates that, once the embryo reaches the blastocyst stage, and assuming that the embryo is judged on examination (124) to be viable, it is removed from the G2.2 medium and prepared for transfer into the uterus. In some laboratories, the G2.2 medium may, optionally, be used for embryo transfer as well. Examination (124) of the embryo may occur in the G2.2 medium or in the oocyte retrieval and handling medium, as described above.

7. Embryo Transfer

The process 100 contemplates that the embryo transfer medium will serve as a carrier for the embryo as it is transferred (126) back into the mother. The embryo will be bathed in the transfer medium, the medium containing the embryo will be drawn into the transfer catheter, the catheter will be inserted into the mother's uterus, guided by an ultrasound probe, and the medium containing the embryo will be injected into the uterus.

8. Cryopreservation

The cryopreservation medium may be used for storing, freezing, thawing, vitrification, and warming the oocyte, prior to fertilization. The same medium may be used for storing, freezing, thawing, vitrification, and warming the cleavage stage embryo, as well as the embryo in the eight to one hundred cell stage.

While the present invention has been described in relation to one embodiment, it will be appreciated that the invention may be utilized in numerous additional embodiments and procedures. Such additional embodiments and procedures are within the scope of the present invention, as defined by the claims which follow.

What is claimed is:

1. A method for performing an in vitro fertilization process, comprising
   a. placing a gamete, zygote or embryo in a first in vitro fertilization medium during a first in vitro fertilization procedure wherein the in vitro fertilization medium comprises:
      (i) water,
      (ii) a buffer present in an amount to buffer the in vitro fertilization medium with physiological pH,
      (iii) ionic constituents present in amounts that support growth and development growth and development of the gamete, zygote or embryo, wherein the ionic constituents include sodium, potassium, calcium and magnesium, and
      (iv) alanyl-glutamine and one or more non-essential amino acids present in amounts to prevent osmotic shock of the gamete, zygote or embryo.

2. The method of claim 1 wherein the in vitro fertilization media further comprises:
   (v) one or more of glucose, lactate and pyruvate present in an amount sufficient to provide a source of energy for the gamete, zygote or embryo.

3. The method of claim 1 wherein the ionic constituents further include phosphate.

4. The method of claim 1 wherein the in vitro fertilization medium further comprises:
   (v) one or more essential amino acids.

5. The method of claim 1 wherein the in vitro fertilization medium further comprises:
   (v) a hormone, one or more growth factors, an antibiotic or one or more vitamins.

6. The method of claim 1 wherein the in vitro fertilization medium further comprises:
   (v) one or more of human serum albumin, hyaluronate, polyvinylpyrolidine, cysteamine, hyaluronidase and glutathione.

7. The method of claim 1 wherein the in vitro fertilization medium comprises the components shown in Table 1 in concentrations shown in column B of Table 1.

8. The method of claim 1 wherein the in vitro fertilization medium comprises the components shown in Table 2 in concentrations shown in column B of Table 2.

9. The method of claim 1 wherein the in vitro fertilization medium comprises the components shown in Table 4 in concentrations shown in column B of Table 4.

10. The method of claim 1 wherein the in vitro fertilization medium comprises the components shown in Table 5 in concentrations shown in column B of Table 5.

11. The method of claim 1 wherein the in vitro fertilization medium comprises the components shown in Table 6 in concentrations shown in column B of Table 6.

12. The method of claim 1 wherein the in vitro fertilization medium comprises the components shown in Table 7 in concentrations shown in column B of Table 7.

13. The method of claim 1 further comprising:
   (b) performing a first in vitro fertilization procedure on the gamete, zygote or embryo in the first in vitro fertilization medium.

14. The method of claim 1 further comprising:
   (b) transferring the gamete, zygote or embryo from the first in vitro fertilization medium into a second in vitro fertilization medium for a second in vitro fertilization procedure, wherein the first and second in vitro fertilization media have different compositions but integrated formulations sharing a core group of ionic and non-essential amino acid constituents thereby minimizing trauma to the gamete, zygote or embryo when they are moved from the first in vitro fertilization medium to the second in vitro fertilization medium.

15. The method of claim 14 further comprising:
   (c) sequentially transferring the gamete, zygote or embryo from the second in vitro fertilization medium into one or more of a third, fourth, fifth, sixth or seventh successive in vitro fertilization medium for one or more of a third, fourth, fifth, sixth or seventh successive in vitro fertilization procedure, wherein the second and third, fourth, fifth, sixth or seventh successive in vitro fertilization media have different compositions but integrated formulations sharing a core group of ionic and non-essential amino acid constituents thereby minimizing trauma to the gamete, zygote or embryo when they are moved into the successive in vitro fertilization medium.

16. The method of claim 1 wherein the first in vitro fertilization procedure is oocyte retrieval and handling, oocyte maturation or oocyte fertilization.

17. The method of claim 1 wherein the first in vitro fertilization procedure is embryonic development to the eight cell stage or embryonic development to the blastocyst stage.

18. The method of claim 1 wherein the first in vitro fertilization procedure is embryo transfer.

19. The method of claim 14 wherein one of the first in vitro fertilization procedure and second in vitro fertilization procedure is cryopreservation of the gamete, zygote or embryo.

* * * * *

(12) INTER PARTES REEXAMINATION CERTIFICATE (0189th)
United States Patent
Gardner et al.

(10) Number: US 6,838,235 C1
(45) Certificate Issued: Sep. 14, 2010

(54) METHODS FOR IN VITRO FERTILIZATION

(75) Inventors: David K. Gardner, Highlands Ranch, CO (US); Michelle Lane, Highlands Ranch, CO (US)

(73) Assignee: Vitrolife AB, Kungsbacka (SE)

Reexamination Request:
No. 95/000,146, Jun. 19, 2006

Reexamination Certificate for:
Patent No.: 6,838,235
Issued: Jan. 4, 2005
Appl. No.: 10/322,914
Filed: Dec. 18, 2002

Related U.S. Application Data

(63) Continuation of application No. 09/201,594, filed on Nov. 30, 1998, now abandoned.

(51) Int. Cl.
*A01N 1/02* (2006.01)

(52) U.S. Cl. .......................... 435/2; 435/366; 435/374; 435/404

(58) Field of Classification Search ........................ None
See application file for complete search history.

(56) References Cited

U.S. PATENT DOCUMENTS

| | | | | |
|---|---|---|---|---|
| 5,326,699 | A | 7/1994 | Torishima et al. | 435/384 |
| 5,328,844 | A | 7/1994 | Moore | 435/240 |
| 5,661,034 | A | 8/1997 | Hayakawa et al. | 435/383 |
| 5,837,543 | A | * 11/1998 | Conway-Myers et al. | 435/373 |
| 5,897,988 | A | * 4/1999 | Huszar | 435/2 |
| 6,132,952 | A | * 10/2000 | Cohen et al. | 435/2 |

FOREIGN PATENT DOCUMENTS

| | | |
|---|---|---|
| CA | 2231148 | 3/1997 |
| CA | 2199663 | 9/1998 |
| EP | 0 220 379 B1 | 5/1987 |

OTHER PUBLICATIONS

Blake et al., The Cochrane Collaboration, pp. 1–80 (Wiley Publishers) (2007).*
Gardner et al., Seminars in Reproductive Medicine, 23 (2005) pp. 319–324.*
Katz–Jaffe et al., Fertility and Sterility, 86(3) pp. 678–685 (Sep. 2006).*
Jul. 25, 2007 Screen Print from Irvine Scientifics webpage.*
Jul. 25, 2007 Screen Print from Medicult webpage.*
Jul. 25, 2007 Screen Print from Sage's webpage.*
Jul. 25, 2007 Screen Print from Cook Medical webpage.*
Morrison & Boyd, "Organic Chemistry" 3rd Ed. (Allyn and Bacon, Inc. 1973) pp. 1133–1135.*
Gardner et al ; "Culture and transfer of human blastocysts increases implantation rates and reduces the need for multiple embryo transfers"; Jan. 1998; pp. 84–88.
Eagle, "The Specific Amino Acid Requirements of a Mammalian Cell (Strain L) in Tissue Culture," Amino Acid Needs of Mammalian Cells, Nov. 19, 1954, pp. 839–852.
Sigma Cell Culture Reagents 1993 Catalogue Price List (published 1992) Sigma Chemical Company, St. Louis, MO, 1992, p. 7.
Atanassov, et al., "Reduction of Ammonia Formation in Cell Cultures by L–alanyl–L–glutamine Requires Optimization of the Dipeptide Concentration," Journal of Biotechnology 62 (1998), pp. 159–161.
Hagemann, et al., "Development of Bovine Embryos in Single In Vitro Production (sIVP) Systems," Molecular Reproduction and Development 51:143–147 (1998).
Christie, et al., "Growth and Metabolism of a Murine Hybridoma in Cultures Containing Glutamine–Based Dipeptides," Life Technologies Focus 16, No. 1, 1994, p. 9.
Quinn, "Human Embryo Culture Media," Embryo Mail Website, Feb. 13, 1997.
Y. Minamoto et al "Development of a Serum–Free and Heat–Sterilizable Medium and Continuous High–Density Cell Culture" 1991, pp. 35–51.
A. Christie et al "Glutamine–Based Dipeptides are utilized in Mammalian Cell Culture by Extracellular Hydrolysis Catalyzed by a Specific peptidase" 1994 pp. 277–290.
M. Scholtes et al "Blastocyst Transfer in Day–5 Embryo Transfer Depends Primarily on the Number of Oocytes Retrieved and not on age" 1998 pp. 78–?.
D. Gardner et al "Culture and Selection of Viable Blastocysts: A Feasible Proposition For Human IVF?"1997 pp. 367–382.

* cited by examiner

*Primary Examiner*—Brenda Brumback

(57) ABSTRACT

Instead of immersing human reproductive cells in a single culture medium throughout the various procedures used in IVF, a process is provided by which the reproductive cells may be moved through a sequence of distinct culture media as the various IVF procedures are carried out. In one implementation, the culture media specifically formulated to provide a physical environment similar to that found within the female reproductive tract and conducive to growth and development of human reproductive cells during the various stages of the IVF process. In this regard, specifically formulated culture media can be applied to support the reproductive cells in one or more of the following procedures: oocyte retrieval and handling; oocyte maturation; ordinary fertilization; oocyte, zygote and embryo examination and biopsy; embryonic development to the eight-cell stage; embryonic development to the blastocyst stage; embryo transfer; and cryopreservation.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-19 are cancelled.

* * * * *